United States Patent [19]

Edgren et al.

[11] Patent Number: 4,503,030
[45] Date of Patent: Mar. 5, 1985

[54] DEVICE FOR DELIVERING DRUG TO CERTAIN PH ENVIRONMENTS

[75] Inventors: David Edgren, El Granada; Patrick S. L. Wong, Hayward; Felix Theeuwes, Los Altos, all of Calif.

[73] Assignee: ALZA Corporation, Palo Alto, Calif.

[21] Appl. No.: 501,573

[22] Filed: Jun. 6, 1983

[51] Int. Cl.³ .......................... A61K 9/24; A61K 9/22; A61K 9/32; A61K 9/36
[52] U.S. Cl. ........................................ 424/15; 424/32; 424/33; 424/34; 424/35
[58] Field of Search ...................... 424/15, 32, 33, 34, 424/35

[56] References Cited

U.S. PATENT DOCUMENTS

| 216,107 | 6/1879 | Richards | 424/15 |
|---|---|---|---|
| 3,089,824 | 5/1963 | Wurster | 167/82 |
| 3,117,027 | 1/1964 | Lindlof et al. | 118/303 |
| 3,146,169 | 8/1964 | Stephenson et al. | 424/15 |
| 3,196,827 | 7/1965 | Wurster et al. | 118/24 |
| 3,207,824 | 9/1965 | Wurster et al. | 264/117 |
| 3,241,520 | 3/1966 | Wurster et al. | 118/62 |
| 3,253,944 | 5/1966 | Wurster | 117/100 |
| 3,620,759 | 11/1971 | Maddox | 424/15 |
| 3,823,816 | 7/1974 | Controulis et al. | 424/15 |
| 3,845,770 | 11/1974 | Theeuwes et al. | 424/15 |
| 3,916,899 | 11/1975 | Theeuwes et al. | 128/260 |
| 4,008,719 | 2/1977 | Theeuwes et al. | 128/260 |
| 4,036,222 | 7/1977 | Theeuwes | 128/260 |
| 4,063,064 | 12/1977 | Saunders et al. | 424/15 |
| 4,077,407 | 3/1978 | Theeuwes et al. | 128/260 |
| 4,088,864 | 5/1978 | Theeuwes et al. | 424/15 |
| 4,093,708 | 6/1978 | Zaffaroni et al. | 424/15 |
| 4,096,238 | 6/1978 | Zaffaroni et al. | 424/15 |
| 4,111,201 | 9/1978 | Theeuwes | 128/260 |
| 4,116,241 | 9/1978 | Theeuwes et al. | 424/15 |
| 4,160,020 | 7/1979 | Ayer et al. | 424/15 |
| 4,218,433 | 8/1980 | Kooichi et al. | 424/15 |

FOREIGN PATENT DOCUMENTS 1372040 10/1974 United Kingdom ................ 424/15

Primary Examiner—Shep K. Rose
Attorney, Agent, or Firm—Paul L. Sabatine; Edward L. Mandell; Steven F. Stone

[57] ABSTRACT

An osmotic device is disclosed for delivering a beneficial agent to a first environment having a pH of 1.0 to 3.5 inclusive and to a second environment having a pH of greater than 3.5 to 8.0. The device maintains its integrity in the first environment and loses its integrity in the second environment.

5 Claims, 6 Drawing Figures

DEVICE FOR DELIVERING DRUG TO CERTAIN PH ENVIRONMENTS

FIELD OF THE INVENTION

This invention pertains to both a novel and useful osmotic device for dispensing a drug to certain pH regions of the gastrointestinal tract. More particularly, the invention relates to an osmotic device comprising a wall formed of a semipermeable pH sensitive composition that surrounds a compartment containing a drug, with a passageway through the wall connecting the exterior of the device with the compartment. The device delivers drug at a controlled rate in the region of the gastrointestinal tract having a pH of less than 3.5, and the device self-destructs and releases all its drug in the region of the gastrointestinal tract having a pH greater than 3.5, thereby providing total availability for drug absorption.

BACKGROUND OF THE INVENTION

Both pharmacy and medicine have sought, since the beginning of antiquity, a delivery system for the controlled administration of a beneficial drug. The first written reference to a delivery system, a dosage form, is in the Eber Papyrus, written about 1552 B.C. The Eber Papyrus mentions dosage forms such as anal suppositories, vaginal pessaries, ointments, oral pill formulations, and other dosage preparations. About 2500 years passed without any advance in dosage form development, until the Arab physician Rhazes, 865-925 A.D., invented the coated pill. About a century later the Persian Avicenna, 980-1037 A.D., coated pills with gold or silver for increasing patient acceptability and for enhancing the effectiveness of the drug. Also, around this time, the first tablet was described in Arabian manuscripts written by Al-Zahrawi, 936-1009 A.D. The manuscripts described a tablet formed from the hollow impressions in two matched-facing tablet molds. Pharmacy and medicine waited about 800 years for the next innovation in dosage forms, when in 1883 Mothes invented the capsule for administering drug. The next quantum and profound leap in dosage forms came in 1972 with the invention of the osmotic delivery device by inventors Theeuwes and Higuchi. This unique osmotic delivery device is manufactured in one embodiment for oral use, and in this embodiment it embraces the appearance of a tablet with a drug delivery portal. It is the first oral dosage form that delivers throughout the entire gastrointestinal tract a known amount of drug per unit time at controlled rate of delivery. The oral osmotic device maintains its physical and chemical integrity during the prolonged period of time it transits the total length of the gastrointestinal tract.

The oral route is the most ancient route of drug administration, and it is the most convenient route for admitting a drug into the systemic circulation. The oral route can be used for administering drugs that are absorbed into systemic circulation from all regions of the gastrointestinal tract including the stomach, small intestine and the large intestine, and it can be used for administering drugs that are absorbed into systemic circulation from certain regions of the gastrointestinal tract, mainly the stomach and the small intestine. The presently available oral, osmotic device delivers drugs that are absorbed from all regions of the gastrointestinal tract. It will be appreciated by those versed in the oral dispensing art in view of this presentation, that a critical and urgent need exists for an osmotic device that can deliver drugs only to certain regions of the gastrointestinal tract. The need exists for an oral osmotic device that can deliver drug to certain regions of the gastrointestinal tract including the stomach and the small intestine for making the maximum amount of drug available for absorption in these drug-absorbing regions. The need exists also for an osmotic device that delivers drug in the region of drug absorption, and concomitantly substantially avoids drug delivery in other regions of the gastrointestinal tract, including the large intestine where the drug may not be absorbed into the systemic circulation.

OBJECTS OF THE INVENTION

Accordingly, in view of the above presentation it is an immediate object of this invention to provide both a novel and useful oral, osmotic drug delivery device that fulfills the critical and urgent need of the dispensing art, and also makes a substantial contribution to the dispensing art by providing a delivery system useful for obtaining better therapy in the management of health and disease.

Another object of the invention is to provide an oral, osmotic drug delivery device that delivers a drug at a controlled rate comprising a known amount per unit of time in the region of the gastrointestinal tract having a pH of less that 3.5, and then delivers all its drug in the immediately continuing region of the gastrointestinal tract having a pH of greater than 3.5.

Another object of the invention is to provide an oral drug delivery device that maintains its physical and chemical integrity and delivers drug at a controlled rate in the stomach, and loses its physical and chemical integrity and delivers all its drug in the small intestine.

Another object of the invention is to provide an oral, osmotic device for delivering drug at a controlled rate in the stomach and delivers all its drug in the small intestine, which device is relatively economical in cost to manufacture, provides the physician with a dependable drug delivery device, and is well-adapted for practical and acceptable patient use.

Yet another object of the invention is to provide an oral, osmotic device comprising a well formed of a semipermeable composition that keeps its integrity and disintegrates in the small intestine.

It is another object to provide an osmotic device that maintains its physical and chemical integrity during the prolonged period of time the device passes through the stomach of a human consisting of a time up to 4 hours, or longer, and then enters the small intestime wherein the device self-destructs as the wall loses its physical and chemical integrity.

Yet another object of the invention is to provide an oral, osmotic device that dispenses drug at a rate controlled by the device in the stomach, and then dispenses the remainder of its drug in the small intestine and in response to the biological environment of the small intestine.

BRIEF DESCRIPTION OF THE DRAWINGS

In the drawings, which are not drawn to scale, but are set forth to illustrate various inventive embodiments of the invention, the drawing figures are as follows.

In the drawing figures and in the specification, like parts in related figures are illustrated by like numbers. The terms appearing earlier in the specification, and in the description of the drawing figures, as wll as embodiments thereof, are further described elsewhere in this disclosure.

DETAILED DESCRIPTION OF THE DRAWINGS

Figure 1:
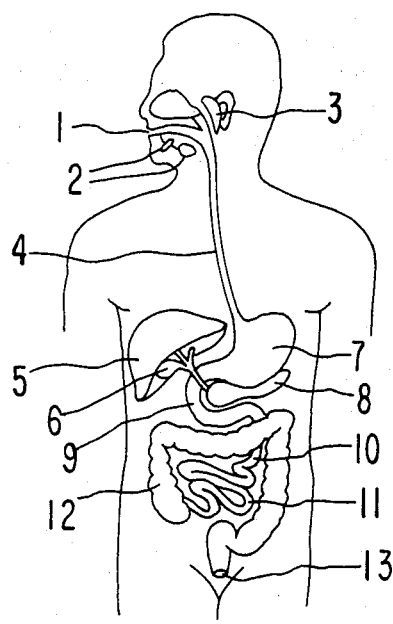
FIG. 1 is a schematic drawing of the gastrointestinal system of a human.

Turning now to the drawing figures in detail, which drawing figures are an example of the oral, osmotic device provided by the invention, and which example is not to be construed as limiting, one example of the oral, osmotic device is seen in FIGS. 1 through 5, considered together.

FIG. 1 is a schematic drawing of the gastrointestinal tract of a human. The gastrointestinal tract comprises a mouth 1, salivary glands 2, parotid gland 3, an esophagus 4, a liver 5, a gall bladder 6, a stomach 7, a pancreas 8, a small intestine consisting essentially of a duodenum 9, a jejunum 10, an ileim 11, a large intestine 12, and an anus 13. Stomach 7 is a biological environment having a pH of from 1.0 to 3.5 inclusive, and the small intestine consisting of duodenum 9, jejunum 10 and ileum 11, is a biological environment having a pH greater than 3.5, usually a pH of greater than 3.5 to 8.0.

Figure 2:
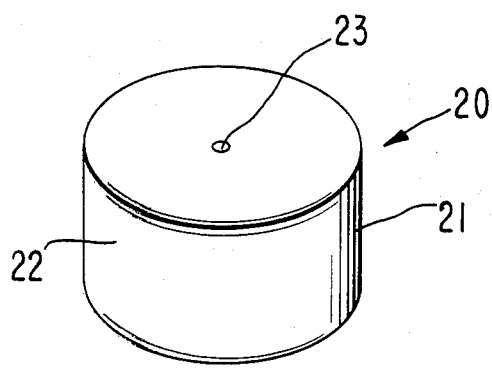
FIG. 2 is a schematic drawing of an oral osmotic device provided by the invention.
Figure 3:
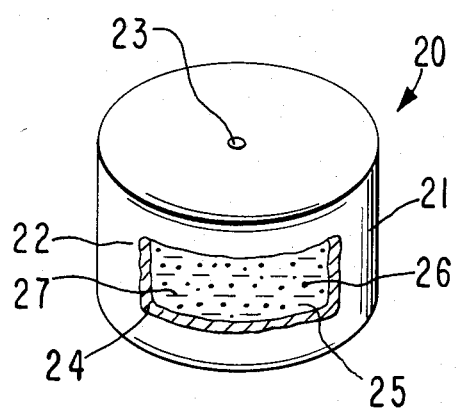
FIG. 3 is a schematic drawing of the oral, osmotic device of FIG. 2 with a section of its wall removed for illustrating the structure of the osmotic device.

FIG. 2 illustrates oral, osmotic device 20 comprising a body 21 sized, shaped and adapted for oral admittance into a gastrointestinal tract having a wall 22 that surrounds an internal compartment seen in FIG. 3. A passageway 23 in wall 22 connects the exterior of osmotic dispenser 20 with the interior of osmotic dispenser 20.

FIG. 3 is the osmotic device 20 of FIG. 2 seen in opened section. In FIG. 3, osmotic device 20 is seen with a portion of wall 22 cut open at 24 for illustrating the internal structure of osmotic device 20. Osmotic device 20 comprises a composite wall formed of a semipermeable polymer and a pH sensitive material. In another embodiment wall 22 comprises a semipermeable polymer, a pH sensitive material and flux enhancer. Wall 22 surrounds and forms an internal compartment 25. Wall 22 comprises a semipermeable polymer that is permeable to the passage of an exterior fluid present in the environment of use and it is substantially impermeable to the passage of drug and other compounds present in compartment 25 or present in the environment of use. Wall 22 also comprises a wall forming material that maintains its physical and chemical integrity in the stomach environment having a pH of 1.0 to 3.5 inclusive, but loses its physical and chemical integrity in the small intestine environment having a pH of greater than 3.5 to 8.0. The materials forming wall 22 are non-toxic to a host.

Compartment 25 houses a beneficial drug 26, identified by dots, that is preferably soluble in an external fluid that is imbibed into compartment 25 and it exhibits an osmotic pressure gradient across wall 22 against an external fluid. In another embodiment, drug 26 has limited solubility in the external fluid that enters compartment 25 and it is mixed with an osmotically effective compound 27, identified by dashes, that is soluble in the external fluid and exhibits an osmotic pressure gradient across wall 22 against an external fluid. Drug 26, present in compartment 25, exhibits its maximum absorption in stomach 7 and the small intestine consisting of duodenum 9, jejunum 10 and ileum 11.

Osmotic device 20 is an environment selective delivery device. Osmotic device 20 possesses two distinct modes of drug delivery, one mode especially adapted for delivering drug 26 at a controlled rate in stomach 7, and one mode especially adapted for total release of drug 26 in the small intestine consisting of duodenum 9, jejunum 10 and ileum 11. Osmotic device 20 delivers drug 26 contained in compartment 25 in stomach 7 by osmotic operations. That is, device 20 delivers drug 26 by fluid being imbibed through semipermeable composite wall 22 into compartment 25, in a tendency towards osmotic equilibrium at a rate determined by the permeability of wall 22 and the osmotic pressure gradient across wall 22, to continuously dissolve drug 26, which drug is hydrodynamically pumped from device 22 through passageway 23 at a controlled and continuous rate over the period of time device 20 travels through stomach 7. That is, the stomach fluid passes through the semipermeable polymer into the compartment to form a solution containing drug that is delivered from the device into the stomach. In the stomach, the wall of the device keeps its integrity, that is, the wall does not undergo dissolution and the wall does not undergo disintegration in the stomach.

Figure 4:
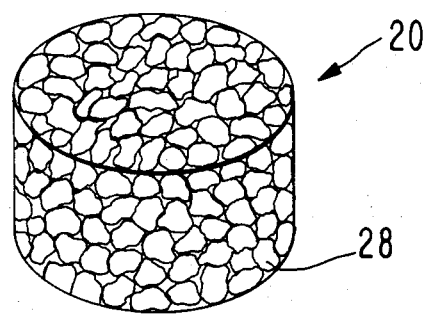
FIG. 4 is a schematic drawing of the oral, osmotic device in the process of undergoing dissolution and disintegration in a biological environment having a pH greater than 3.5.
Figure 5:
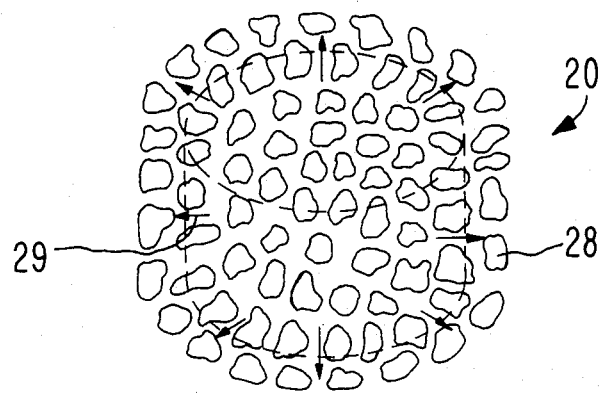
FIG. 5 is a schematic drawing taken in conjunction with the drawing figure of FIG. 4, illustrating the oral, osmotic device in the advance stage of dissolution and disintegration for releasing all its drug to the biological environment having a pH greater than 3.5; and, FIG. 6 is a graph that indicates the release rate profile for one delivery system provided by this invention.

Osmotic device 20 releases all of its remaining drug in the small intestine by the operations depicted in FIG. 4 and in FIG. 5. That is, device 20, on entering into the small intestine, and in direct response to the environment of the small intestine having a pH greater than 3.5, loses its physical and chemical integrity. Device 20, as seen in FIG. 4, breaks up or it dissolves into unconnected, nontoxic portions 28. This dramatic change in physical and chemical structure of wall 22 is caused by the material sensitive to a change in pH in wall 22, disintegrating, dissolving, or being leached from wall 22. These actions, taken as a single operation, or taken as a multiplicity of operations, result in the complete disintegration and dissolution of device 20 as seen in FIG. 5. In FIG. 5, arrows 29 indicate the total break up of device 20 with the accompanying release of all its remaining drug into the small intestine.

Osmotic device 20 of FIGS. 1 through 5 can be made into many embodiments for oral use. The oral device is useful for delivering a drug in the stomach and for delivering drug in the small intestine. The osmotic, oral therapeutic device can have various conventional shapes and sizes such as round with a diameter of ⅛ inches to 9/16 inches, or it can be shaped like a capsule having a range of orally administrable sizes from triple zero to zero, and from 1 to 8, and the like.

DETAILED DESCRIPTION OF THE INVENTION

In attaining the objects, features, and advantages of this invention, it has now been found an osmotic device can be provided for dispensing drug in the stomach followed by dispensing drug in the small intestine, according to the mode and the manner of the invention. The osmotic device comprises a wall that surrounds and defines a compartment. The compartment contains a drug, and optionally an osmotically effective solute. There is a passageway in the wall for dispensing drug from the device when the device is in the stomach.

The wall of the osmotic dispenser is formed of a composite consisting essentially of wall-forming materials that do not adversely affect the drug, the compound, or the biological environment of use. The wall is formed of a composition comprising a selectively permeable polymeric material, and at least one material that keeps its integrity in the stomach, but undergoes change in the pH environment of the small intestine. The materials forming the wall are homogeneously, or heterogeneously blended or dispersed in a wall forming composition in operable relation to yield an osmotically functioning, disintegrating wall.

The selectively permeable materials useful for manufacturing the wall are semipermeable polymers including semipermeable homopolymers, semipermeable copolymers, and the like. In one presently preferred embodiment, typical materials include cellulose esters, cellulose ethers, and cellulose ester-ethers. The cellulosic polymers have a degree of substitution, D.S., on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, alkenyl, aroyl, alkyl, alkoxy, halogen, carboalkyl, alkylcarbamate, alkylcarbonate, alkylsulfonate, alkylsulfamate, and the like semipermeable polymer forming groups.

Representative semipermeable polymers include a member selected from the group consisting of cellulose acylate, cellulose diacylate, cellulose triacylate, cellulose acetate, cellulose diacetate, and cellulose triacetate. Exemplary semipermeable polymers include cellulose acetate having a D.S. of 1.8 to 2.5 and an acetyl content of 32 to 39.8%; cellulose diacetate having a D.S. of 1 to 2 and an acetyl content of 21 to 35%; cellulose triacetate having a D. S. of 2 to 3 and an acetyl content of 35 to 44.8%, and the like. More specific cellulose polymers include cellulose propionate having a D.S. of 1.8 and a propionyl content of 38.5%; cellulose acetate pripionate having a propionyl content of 1.5 to 7% and an acetyl content of 39 to 42%; cellulose acetate propionate having an acetyl content of 2.5 to 3%, a propionyl content of 39.2 to 45%, and a hydroxyl content of 2.8 to 5.4%; cellulose acetate butyrate having a D.S. of 1.8, an acetyl content of 13 to 15 and a butyryl content of 34 to 39%; cellulose acetate butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate, and the like; mixed cellulose esters such as cellulose acetate valerate, cellulose acetate succinate, cellulose propionate succinate, cellulose acetate octanoate, cellulose valerate palmitate, cellulose acetate heptonate, and the like. The semipermeable polymers are disclosed in U.S. Pat. Nos. 3,845,770; 3,916,899; 4,008,719; 4,036,228; 4,077,407; and in 4,111,210.

Additional semipermeable polymers include cellulose acetaldehyde dimethyl acetate; cellulose acetate ethylcarbamate; cellulose acetate methylcarbamate; cellulose dimethylaminoacetate; semipermeable polyamides, semipermeable polyurethanes; semipermeable sulfonated polystyrenes; semipermeable polymers as disclosed by Loeb and Sourirajan in U.S. Pat. No. 3,133,132, and the like. The polymers are known to the art in U.S. Pat. No. 4,160,020, and in *Handbook of Common Polymers* by Scott and Roff, 1971, published by CRC Press, Cleveland Ohio.

The pH sensitive materials useful for blending with the semipermeable polymer for forming wall 22 are materials that keep their physical and chemical integrity in the stomach and lose their physical and chemical integrity in the small intestine. That is, the materials keep their integrity and maintain the integrity of wall 22 in a biological environment having a pH of 1.0 to 3.5 inclusive, and they lose their integrity causing wall 22 to lose its integrity in a biological environment having a pH greater than 3.5 to 8.0. For the purpose of this invention, the expression the material loses its integrity generically denotes the material dissolves, disintegrates, degrades, hydrolyzes, solubilizes, is digested, or it undergoes a like change in a biological environment at a pH greater than 3.5 to 8.0, thereby resulting in device 20 undergoing a similar change and consequently releasing all the remaining drug in the small intestine. The product produced on the change of wall 22 is nontoxic, chemically inert, and physiologically inactive. In operation, the pH sensitive material keeps its integrity and provides structural support for wall 22 during the period of time device 20 is in the stomach and travels therethrough. Then, as osmotic device 20 passes into the small intestine, wall 22 loses its structural integrity and device 20 releases all of drug 26 into the small intestine.

Examples of materials that keep their integrity at a pH of 1.0 to 3.5, but undergo change at a pH greater than 3.5 include, (a) polymers having at least one acidic group that enables the material to keep its integrity in the lower pH environment, (b) polymers that undergo change in the higher pH environment caused by enzymes present in that environment, (c) polymer compositions comprising a polymer and another agent that promotes at the higher pH the disintegration of the wall, such as a polymer and a fat, fatty acid, wax and the like, and (d) polymeric compositions comprising a polymer and agents such as bile, and cholesterol, or the like that form complexes that disintegrate in the higher pH environment and concomitantly release the drug from the device.

Representative of polymers that keep their integrity at a pH of 1.0 to 3.5 inclusive are polyacidic polymers having acid groups in an undissociated form in this pH range, such as vinyl derivatives of partially hydrolyzed styrene-maleic anhydride copolymer, methylmethacrylate-methacrylic acid copolymer, polymethacrylic acid ester, methylacrylate-methacrylic acid ester, partial alkylene glycol ether esters of $C_1$ to $C_7$ alkyl acrylate unsaturated carboxylic acid anhydride copolymers including maleic, citraconic, or itaconic carboxylic acid anhydride, and the like.

Representative of additional polymers that keep their integrity at a pH of 1.0 to 3.5 inclusive, but undergo change in integrity at a pH greater than 3.0 are certain cellulose carboxylic acid esters, and certain carboxylic acid ethers, such as cellulose ethyl phthalate, cellulose acetate phthalate, starch acetate phthalate, amylose acetate phthalate, hydroxypropyl methylcellulose phthalate, amylose acetate phthalate, hydroxypropyl ethylcellulose phthalate, hydroxybutyl methylcellulose phthalate, and other materials such as cellulose acetate hexahydrophthalate, hydroxypropyl methylcellulose hexahydrophthalate, and the like.

Representative of other polymers and polymer compositions comprising at least two ingredients operable for the present purpose of keeping their integrity in the pH range of 1.0 to 3.5 inclusive, but undergoes change in the pH range of 3.5 to 8.0 are polymers such as shellac, ammoniated shellac, formalized gelatin, polyvinyl acetate phthalate, polyvinyl acetate hydrogenphthalate, and the like; and polymer compositions such as a mixture of hydroxypropyl methylcellulose phthalate and ammoniated shellac in a weight to weight ratio of 99 to 1, shellac-formalized gelatin composition, styrene-maleic acid copolymer dibutyl phthalate composition, styrene-maleic acid polyvinyl acetate phthalate composition, shellac-stearic acid composition, and the like. The amount of a pH sensitive material present in the wall is at least 50% by weight, when the wall comprises a semipermeable polymer and a material that is pH sensitive and a semipermeable polymer.

Wall 22 in another embodiment can comprise a flux enhancer, in addition to the semipermeable polymer and the pH sensitive material. The flux enhancers suitable for the present purpose are in a preferred embodiment water soluble polymers selected from the group consisting of hydroxypropyl cellulose, hydroxypropyl methylcellulose, hydroxyethyl cellulose, ethylmethylcellulose, methylcellulose, polyvinyl pyrrolidone, alkylated vinylpyrrolidone polymers, poly(vinyl pyrrolidone-vinyl acetate) copolymer, vinylpyrrolidone-dimethylaminoethylmethylacrylate copolymer, polyethylene glycol, polyethylene oxide, glycerin, and the like. The amount of flux enhancer in a wall is about 5 to 50% by weight. When a flux enhancer is present in the wall with a pH sensitive material, the amount of pH sensitive material for this composition is about 20 to 70% by weight, with the remainder of the wall a semipermeable polymer of 25 to 50% by weight, with the total weight of all wall forming materials 100% by weight. In a presently preferred embodiment the amount of pH sensitive material in the wall is at least 50%, and the amount of composition comprising both a pH sensitive material and a flux enhancer is at least 50%. The wall of the device is unexpected in that it maintains its physical and chemical integrity in a pH up to 3.5 while comprising the pH sensitive material and the composition of the pH sensitive material and flux enhancer in the stated amounts.

In the specification and the accompanying claims, the term drug includes inorganic and organic drugs that are absorbed in the stomach and the small intestine. The drugs include drugs that act on the nervous system, depressants, hypnotics, sedatives, psychic energizers, tranquilizers, anticonvulsants, muscle relaxants, antiparkinsons, analgesics, anti-inflammatory, anesthetics, muscle contractants, antimicrobiols, antimalarials, hormones, contraceptives, sympathomimetics, diuretics, antiparasites, neoplastics, hypoglycemics, ophthalmics, electrolytes, cardiovascular, blood pressure regulating drugs, antiulcer, histamine antagonists, and the like.

Representative of drugs that can be administered in the stomach and in the small intestine include hycanthone, aminophylline, aminosalicylic acid, sulfoxone sodium, erythromycin estolate, erythromycin, orenzyme, carbomycin, riboflavin, thiamine, vitamin $D_2$, vitamin $D_3$, vitamin $B_{12}$, phenylbutazone, acetylsalicylic acid, xanthone, thioxanthone, morphine, codeine, 5-fluorouracil, 5-bromouracil, benzomethamine, oxphenonium, hexamethonium, tubocurarine, atropine, folic acid and the like. The drugs are known in the art in *Pharmaceutical Sciences*, by Remington, 1980, published by Mack Publishing Co.; *Physicians' Desk Reference*, 36th Edition, 1982, published by Medical Economics Co.; and *Medicinal Chemistry*, 3rd Edition, Vol 1 and 2, by Burger, published by Wiley-Interscience Co. The amount of drug present in a device will vary depending on the activity and the amount of drug to be administered to the host. Generally, the osmotic device will contain from 0.05 ng to 3 g, or more, with individual devices containing 5 mg, 25 mg, 50 mg, 125 mg, 250 mg, 500 mg, and the like.

The expression passageway as used herein includes an aperture, orifice, bore, hole or the like through the wall. The expression includes also an erodible element in the wall such as a gelatin plug that erodes and forms a passageway in the environment of use. A detailed description of osmotic passageways, and the maximum and minimum dimensions for the passageway are disclosed in U.S. Pat. Nos. 3,845,770 and 3,916,899

The osmotic passageway has a maximum cross sectional area $A_s$ defined by $$\frac{L}{F} \times \frac{Q_p}{t} \times \frac{1}{DS}$$

wherein L is the length of the passageway $Q_p/t$ is the mass delivery rate of the agent, D is the diffusion coefficient of the agent, S is the solubility of the agent in the fluid, and F is from 2 to 1000, said passageway having a minimum area $A_s$ defined by $$\left[ \frac{Lv}{t} \times 8 \times \frac{\pi \eta}{\Delta P} \right]^{\frac{1}{2}}$$

wherein L is the length of the passageway, v/t is the agent solution volume delivery rate, $\pi$ is 3.14; $\eta$ is the viscosity of agent solution dispensed from the device and $\Delta P$ is the hydrostatic pressure difference between the inside and the outside of the compartment having a valve up to 20 atmospheres.

The expression "osmotically effective compound" as used herein includes inorganic and organic compounds that are effective solutes that exhibit an osmotic pressure gradient across the wall of the dispenser against an external fluid. The osmotic solutes are used conveniently by homogenously or heterogenously mixing a solute with the active drug in the compartment of the osmotic device. In operation, these solutes osmotically attract and imbibe fluid into the compartment to produce a solution of the solute which is osmotically dispensed from the device concomitantly transporting therewith dissolved and undissolved drug. Various osmotically effective solutes include compounds such as magnesium sulfate, magnesium chloride, sodium chloride, potassium sulfate, sodium sulfate, mannitol, urea, inositol, succrose, glucose and the like. The amount of osmotic solute in an osmotic device is from about 0.5 mg to 500 mg, or more.

The osmotic device is manufactured by mixing the ingredients present in a compartment by ballmilling, calendering, stirring, and pressing it into a preselected shape. The materials forming the wall are blended into a composition and applied by dipping, molding or spraying the pressed drug core. One procedure for applying the wall is the air suspension technique. The air suspension technique can be used for manufacturing a wall as described in U.S. Pat. No. 2,799,341; in *J. Am. Pharm. Assoc.*, Vol. 48, pages 451 to 459, 1959; and in *J. Am. Pharm. Assoc.*, Vol. 49, pages 82 to 84, 1960.

The solvents used for forming the wall include water, ketones, esters, ethers, alcohols, aliphatic hydrocarbons, halogenated solvents, cycloaliphatics, aromatics, heterocyclic solvents, and mixtures thereof. Typical solvents include acetone, diacetone, methanol, ethanol, isopropyl alcohol, methyl isobutyl ketone, n-heptane, methylene dichloride, ethylene dichloride, mixtures such as acetone and water, ethanol and water, acetone and ethyl alcohol, methylene dichloride and methanol, ethylene dichloride and methanol, and the like.

The following example is merely illustrative of the present invention, and it should not be considered as limiting the scope of the invention in any way, as this example, and other equivalents thereof will become more apparent to those versed in the pharmaceutical and medical dispensing arts in the light of the present disclosure, the drawings, and the accompanying claims.

EXAMPLE 1

An oral, osmotic device for delivering the beneficial drug hydralazine in the stomach and in the small intestine is manufactured as follows: a drug formulation is prepared for housing in the compartment of the device by forming drug cores weighing 275 mg and consisting essentially of 18.2 wt% hydralazine hydrochloride, 75.9 wt % mannitol, 2.9 wt % hydroxypropyl methylcellulose, and 3 wt % stearic acid, which are blended into a homogeneous drug formulation, and a precompartment formed by compressing the mass in a ⅜ inch standard concave punch in a Manesty press at 1.5 tons pressure head.

Figure 6:
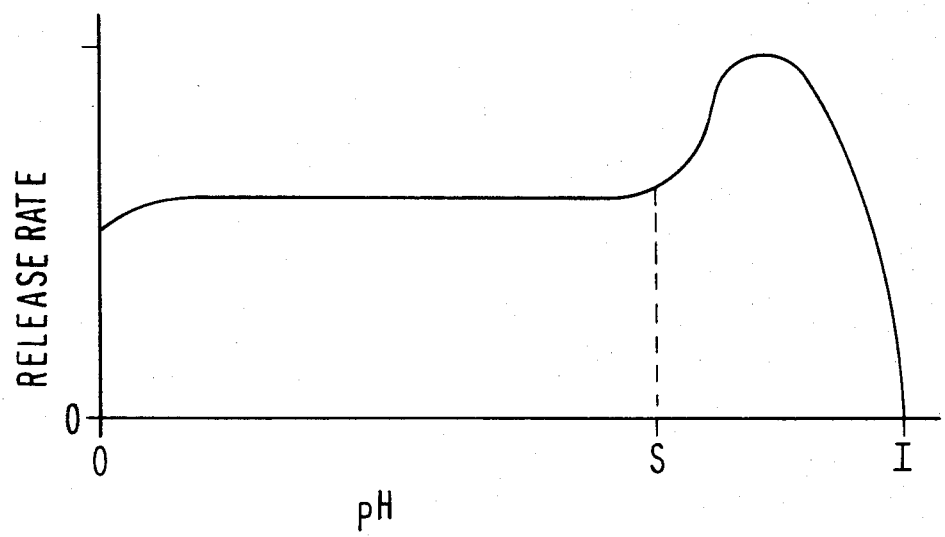

Next, the compressed drug core is placed in an air suspension coating machine and coated with a semipermeable pH sensitive composition consisting of 25% by weight of cellulose acetate having an acetyl content of 32%, 25% by weight of cellulose acetate having an acetyl content of 39.8%, and 50% by weight of hydroxypropyl methylcellulose phthalate. The wall forming composition is applied from a solution of 5% by weight of solids in a solvent system consisting essentially of 1900 g methylene chloride and 1900 g of methanol. The osmotic devices are coated to a wall weight of approximately 20 mg and air dried in an oven at 50 C. for 48 hours. A 10 mil passageway is laser drilled through the wall to complete fabrication of the osmotic device. FIG. 6 depicts the simulated release rate profile for the osmotic device. The figure depicts the release profile consisting of a substantially zero rate in a pH of 1.0 to 3.5 indicated from time 0 to S, which is followed by a complete release of drug in a pH greater than 3.5 as indicated from time S to T.

EXAMPLE 2

An oral, osmotic device is made by following the above procedure with all conditions as set forth, except that in this example the device comprises a different wall-forming composition. In this example, the wall composition consists of 30% cellulose acetate having an acetyl content of 39.8%, 30% hydroxypropyl methylcellulose, and 40% hydroxypropyl methylcellulose phthalate. The device has a 7.5 mil passageway, and it keeps its integrity in a pH of 1.0 to 3.5 inclusive and it loses its integrity in a pH of from 3.5 to 8.0.

The osmotic device can be used for delivering a beneficial drug to two different pH environments at two different release rate profiles. The device thus provides a unique method for obtaining the maximum therapeutic benefit of the drug. The method comprises: (I) admitting into a first environment and a second environment an osmotic drug delivery device comprising: (a) a shaped wall formed of a composition comprising (1) a semipermeable material that is permeable to the passage of an exterior fluid, impermeable to the passage of drug and keeps its physical and chemical integrity in the first and second environments, and (2) a pH sensitive material that is permeable to the passage of fluid, impermeable to the passage of drug, keeps its physical and chemical integrity in the first environment and loses its physical and chemical integrity in the second environment causing the osmotic device to undergo a complete loss of shape, size and structure, which wall surrounds and defines; (b) a composition containing a beneficial drug that is administrable in the first and second environment; (c) a passageway in the wall connecting the compartment and the exterior of the device for delivering drug from the device; (2) imbibing fluid into the compartment through the wall at a rate determined by the permeability of the wall and the osmotic pressure gradient across the wall to form a solution containing drug; (3) delivering the drug through the passageway to the first environment at a controlled rate of release over a prolonged period of time, with the device then passing into the second environment; and, (4) delivering all the remaining drug in the second environment at a substantially instant rate of release over a short period of time; thereby obtaining the beneficial effect of the drug in the first and second environments.

While there has been described and pointed out novel features of an osmotic device and novel features for delivering a drug, it is to be understood those versed in the art will appreciate that various modifications, changes and omissions can be made without departing from the spirit of the invention.

We claim:

1. An oral osmotic device for the delivery of a beneficial agent to the stomach as a first environment of use and to the intestine as a second environment of use, the device comprising:
   (a) a shaped wall formed of (1) a semipermeable material that is permeable to the passage of an exterior fluid, substantially impermeable to the passage of agent, and maintain its physical and chemical integrity in both the first and second environment, said semipermeable material a member selected from the group consisting of a cellulose ester, cellulose ether, cellulose ester-ether, cellulose acylate, cellulose diacylate, cellulose triacylate, cellulose acetate, cellulose diacetate, cellulose triacetate, and cellulose diesters, and blended therewith (2) a pH sensitive material that is permeable to the passage of an exterior fluid, substantially impermeable to the passage of agent, maintains its physical and chemical integrity in the first environment and loses its physical and chemical integrity in the second environment, said material a member selected from the group consisting of cellulose carboxylic acid ester, cellulose carboxylic acid ether, cellulose ethyl phthalate, cellulose acetate phthalate, starch acetate phthalate, amylose acetate phthalate, hydroxypropyl methylcellulose phthalate, hydroxypropyl ethylcellulose phthalate, hydroxybutyl methylcellulose phthalate, cellulose acetate hexahydrophthalate, and hydroxypropyl methylcellulose hexahydrophthalate;

(b) a compartment containing a dosage unit amount of a beneficial agent;

(c) a passageway through the wall connecting the compartment with the exterior of the device, the passageway having a maximum cross-sectional area, $A_s$ defined by $$\frac{L}{F} \times \frac{Q_p}{t} \times \frac{1}{DS}$$

wherein L is the length of the passageway ($Q_p/t$) is the mass delivery rate of the agent, D is the diffusion coefficient of agent, S is the solubility of agent in the fluid, and F is from 2 to 1000, said passageway having a minimum area $A_s$ defined by $$\left[ \frac{Lv}{t} \times 8 \times \frac{\pi \eta}{\Delta P} \right]^{\frac{1}{2}}$$

wherein L is the length of the passageway, v/t is the agent solution volume delivery rate, $\pi$ is 3.14, $\eta$ is the viscosity of the agent solution dispensed from the osmotic device, and $\Delta P$ is the hydrostatic pressure difference between the inside and the outside of the compartment having a value up to 20 atmospheres; and (d) wherein, when the osmotic device is in the first environment, the device maintains its integrity and delivers agent through the passageway at a controlled rate over a prolonged period of time, and when the device is in operation in the second environment, the device loses its integrity and delivers the remaining agent in a short period of time.

2. The osmotic device for the delivery of the beneficial agent to the environments of use according to claim 1, wherein the agent is a drug that is administrable in the stomach and in the small intestine.

3. The osmotic device for the delivery of the beneficial agent to the environments of use according to claim 1, wherein the wall additionally comprises a flux enhancer that is soluble in the first and second environment.

4. The oral osmotic device for the delivery of a beneficial agent according to claim 1, wherein the material that loses its integrity in the second environment is replaced by a member selected from the group consisting of styrene-maleic anhydride copolymer, methylmethacrylate-methacrylic acid copolymer, polymethacrylic acid ester, methylacrylate-methacrylic acid ester, and carboxylic acid anhydride copolymer.

5. The oral osmotic device for the delivery of the beneficial agent according to claim 1, wherein the material that loses its integrity in the second environment is replaced by a member selected from the group consisting of shellac, ammoniated shellac, shellac-formalized gelatin, shellac-stearic acid, styrenemaleic acid copolymer dibutylphthalate, and styrene-maleic acid polyvinyl acetatephthalate.

* * * * *